US009782198B2

(12) United States Patent
Elhawary et al.

(10) Patent No.: US 9,782,198 B2
(45) Date of Patent: Oct. 10, 2017

(54) LOCALIZATION OF ROBOTIC REMOTE CENTER OF MOTION POINT USING CUSTOM TROCAR (71) Applicant: KONINKLIJKE PHILIPS N.V., Eindhoven (NL)

(72) Inventors: Haytham Elhawary, New York, NY (US); Aleksandra Popovic, New York, NY (US); Ameet Kumar Jain, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 42 days.

(21) Appl. No.: 14/779,997

(22) PCT Filed: Mar. 21, 2014

(86) PCT No.: PCT/IB2014/060020
§ 371 (c)(1),
(2) Date: Sep. 25, 2015

(87) PCT Pub. No.: WO2014/155257
PCT Pub. Date: Oct. 2, 2014

(65) Prior Publication Data
US 2016/0045269 A1    Feb. 18, 2016

Related U.S. Application Data (60) Provisional application No. 61/805,947, filed on Mar. 28, 2013.

(51) Int. Cl.
A61B 17/34    (2006.01)
A61B 34/20    (2016.01)
(Continued)

(52) U.S. Cl.
CPC ............ *A61B 17/34* (2013.01); *A61B 19/201* (2013.01); *A61B 19/2203* (2013.01);
(Continued)

(58) Field of Classification Search
CPC ......... A61B 34/20; A61B 34/30; A61B 34/70; A61B 90/11; A61B 90/10
(Continued)

(56) References Cited

U.S. PATENT DOCUMENTS 3,577,982 A * 5/1971 La Par .................... A61F 5/442
                                                            600/435
5,951,475 A    9/1999 Gueziec et al.
(Continued)

FOREIGN PATENT DOCUMENTS

WO    2011149260 A2    12/2011

OTHER PUBLICATIONS

Nathanael Kuo et al, "Automatic segmentation of radiographic fiducial and seeds from X-ray images in prostate brachytherapy", Published in final edited form as: Med Eng Phys. Jan. 2012; 34(1); pp. 64-77. doi:10.1016/j.medengphy. 2011.06.019.
(Continued)

Primary Examiner — Timothy Waggoner (57) ABSTRACT

A system for providing a remote center of motion for robotic control includes a marker device (104) configured to include one or more shapes (105) to indicate position and orientation of the marker device in an image collected by an imaging system (110). The marker device is configured to receive or partially receive an instrument (102) therein, the instrument being robotically guided. A registration module (117) is configured to register a coordinate system of the image with that of the robotically guided instrument using the marker device to define a position in a robot coordinate system (132) where a virtual remote center of motion (140) exists. Control
(Continued)

software (136) is configured to control a motion of the robotically guided instrument wherein the virtual remote center of motion constrains the motion of a robot (130).

17 Claims, 4 Drawing Sheets

(51) Int. Cl.
    *A61B 19/00*     (2006.01)
    *A61B 90/00*     (2016.01)
    *A61B 34/30*     (2016.01)

(52) U.S. Cl.
    CPC .............. *A61B 19/54* (2013.01); *A61B 34/20* (2016.02); *A61B 34/30* (2016.02); *A61B 90/39* (2016.02); *A61B 17/3421* (2013.01); *A61B 2019/5466* (2013.01); *A61B 2034/301* (2016.02); *A61B 2090/364* (2016.02); *A61B 2090/3966* (2016.02); *A61B 2090/3991* (2016.02)

(58) Field of Classification Search
    USPC ........................................................ 604/264
    See application file for complete search history.

(56) References Cited

U.S. PATENT DOCUMENTS

| | | | |
|---|---|---|---|
| 7,021,173 B2 | 4/2006 | Stoianovici et al. | |
| 7,175,631 B2 | 2/2007 | Wilson et al. | |
| 7,824,414 B2 * | 11/2010 | Evans | A61F 2/442 |
| | | | 606/151 |
| 9,066,737 B2 * | 6/2015 | Barwinkel | A61B 19/201 |
| 9,398,930 B2 * | 7/2016 | Leung | A61B 18/02 |
| 2007/0173976 A1 | 7/2007 | Schena | |
| 2008/0269602 A1 * | 10/2008 | Csavoy | A61B 90/18 |
| | | | 600/426 |
| 2012/0158031 A1 | 6/2012 | Mccawley | |

OTHER PUBLICATIONS

E. Moult et al, "Automatic C-arm Pose Estimation via 2D/3D Hybrid Registration of a Radiographic Fiducial", Proc. SPIE, vol. 7964, 79642S-1, http://spiedl.org/terms.

Ameet Kumar Jain et al, "A robust fluoroscope tracking fiducial", Medical Physics, vol. 32, No. 10, Oct. 2005, pp. 3185-3198.

* cited by examiner

LOCALIZATION OF ROBOTIC REMOTE CENTER OF MOTION POINT USING CUSTOM TROCAR

CROSS-REFERENCE TO PRIOR APPLICATIONS

This application is the U.S. National Phase application under 35 U.S.C. §371 of International Application No. PCT/IB2014/060020, filed on Mar. 21, 2014, which claims the benefit of U.S. Provisional Patent Application No. 61/805,947, filed on Mar. 28, 2013. These applications are hereby incorporated by reference herein.

BACKGROUND

Technical Field

This disclosure relates to medical instruments and robotic control thereof and more particularly to defining a remote center of motion for software based robots for medical procedures.

Description of the Related Art

Rotational X-ray C-arms are used in various interventional and surgical suites to acquire 2D and 3D images of an anatomy of interest. Minimally invasive surgery is performed using elongated instruments inserted into a patient's body through small ports. In robotic guided minimally invasive surgery, it is critical to not exert any translational force on the port, as this may cause injury to the patient. A remote center of motion (RCM) is a point that facilitates motion of an end-effector (medical device) inside the patient with zero motion at the RCM point. The RCM point needs to coincide with the insertion point for medical robots. However, conventional methods require manual entry of a point indicating to the system the location of the desired remote center of motion in a reference frame of the robot.

Surgeons who perform robotic guided surgery with systems that do not have an implicit remote center of motion in the mechanism design need to manually enter a position to impose a virtual remote center of motion to the robot arm. However, this can lead to errors and translate to difficulties during surgery.

SUMMARY

In accordance with the present principles, a system for providing a remote center of motion for robotic control includes a marker device configured to include one or more shapes to indicate position and orientation of the marker device in an image collected by an imaging system. The marker device is configured to receive or partially receive an instrument therein, the instrument being robotically guided. A registration module is configured to register a coordinate system of the image with that of the robotically guided instrument using the marker device to define a position in a robot coordinate system where a virtual remote center of motion exists. Control software is configured to control a motion of the robotically guided instrument wherein the virtual remote center of motion constrains the motion of a robot.

A marker for providing a remote center of motion for robotic control includes a radiolucent wall forming an internal cavity configured to receive or partially one or more instruments; and a radio-opaque material formed on or in the wall, the material being configured into one or more geometric shapes to indicate a three-dimensional orientation and position of the marker in an X-ray image such that the three-dimensional orientation and position provide a virtual remote center of motion for robotic control for the one or more instruments.

A method for providing a remote center of motion for robotic control includes placing a marker at a location relative to a subject, the marker being configured to include one or more shapes to indicate position and orientation of the marker in an image; imaging the marker; registering a coordinate system of the image with that of a robotically guided instrument using the marker to define a position in a robot coordinate system where a virtual remote center of motion exists; and controlling a motion of the robotically controlled instrument wherein the virtual remote center of motion constrains the motion of a robot.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

This present embodiments provide systems and methods for determining and/or creating a virtual remote center of motion (RCM) for robotic control. For robotic devices that do not have a remote center of motion inherent in its mechanism design, software capabilities are needed to define a virtual point in space along a robot end effector, such that the robot control software can calculate the necessary motions of the robot to avoid exerting translational forces at that point in space. One feature includes a radiolucent marker integrated in or attached to a trocar, port or other instrument allowing X-ray image-based detection of a remote center of motion of a surgical instrument (e.g., a laparoscopic instrument) held by a robot. Another feature includes a method to compute a position of the remote center of motion in a robot coordinate frame. In accordance with the present principles, fast and operator-independent detection of the remote center of motion from a single X-ray image is provided. Accurate determination of the RCM is one important aspect for safety of a patient during robotic manipulation of instruments.

The present principles will illustratively concentrate on clinical applications where robotic guided minimally invasive surgery is performed under X-ray C-arm and/or endoscopy guidance. However, these example applications are non-limiting and other imaging techniques of medical instruments may benefit and be employed in accordance with the present principles. For example, the present embodiments can be employed in any minimally invasive procedure performed in an operating room or elsewhere including a cardiac suite, an oncological suite, neurosurgical suite, etc.

It should be understood that the present invention will be described in terms of medical instruments; however, the teachings of the present invention are much broader and are applicable to any robotically controlled instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
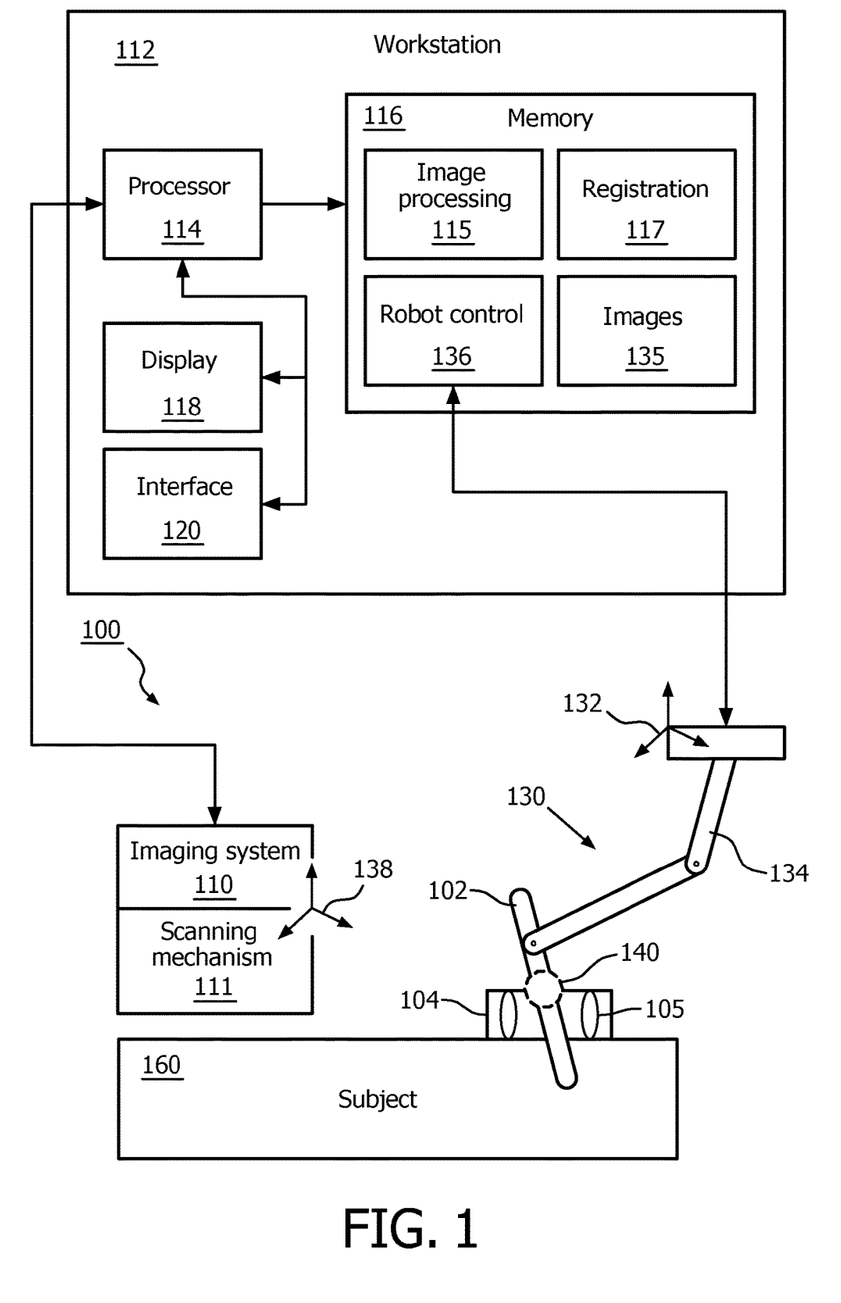
FIG. 1 is a block/flow diagram showing a system for providing a virtual remote center of motion in accordance with one embodiment.

Referring now to the drawings in which like numerals represent the same or similar elements and initially to FIG. 1, a system 100 is shown for providing and/or determining a remote center of motion (RCM). System 100 may include a workstation or console 112 from which a procedure is supervised and/or managed. Workstation 112 preferably includes one or more processors 114 and memory 116 for storing programs and applications. Memory 116 may store an image processing module 115 configured to interpret images from an imaging system 110 to decipher a position of a marker device 104. Image processing module 115 is configured to use the image feedback (and any other feedback, e.g., electromagnetic (EM) tracking) to determine a position and orientation of the marker device 104. The device 104 may be positioned on a subject (e.g., patient) 160 or may include a port of other devices where medical devices or instruments 102 enter the subject 160. The device 104 may include a trocar or other port or may include a separate part that fits in or on the trocar or port. The marker device 104 is positioned or placed at an interface and receives or partially receives an instrument 102 therein. The marker device 104 may include an annulus or other object having an internal cavity configured to act as a port. In one embodiment, the marker device 104 is fixed at a particular position, e.g., at a port entry position into the body of a patient, etc. The medical device 102 is robotically controlled and may include a catheter, a guidewire, a probe, an endoscope, another robot, an electrode, a filter device, a balloon device, or other medical component, etc.; however, the present principles are particularly useful when a rigid instrument is employed.

A robot system 130 includes a coordinate system 132. The robot system 130 is controlled using the processor 114 and memory 116, although a separate control system may be employed. The robot system 130 includes a robot arm 134 configured to grasp and hold the medical instrument 102. The robot system 130 and, in particular, the robot arm 134 are controlled using control software 136 stored in memory 116. The control software 136 is supplied rules, constraints and motions, (e.g., from a program, plan or interface 120) that are permissible and needed to carry out a procedure.

The imaging system 110 includes an intraoperative X-ray system. In one embodiment, the imaging system 110 includes a scanning system or mechanism 111, e.g., a dual or single C-arm or any similar device that can produce 2D or 3D intraoperative images. In a particularly useful embodiment, the mechanism 111 may include a C-arm or other positioning system for imaging. Although X-rays are described as an imaging modality, other modalities may also be employed, such as magnetic resonance, computed tomography, ultrasound, etc.

The memory 116 includes a registration module 117 that receives an image(s) 135, which include the device 102 and device 104 therein from the imaging system 110 and/or from the image processing module 115. The registration module 117 registers the images 135 with positions of the robotic coordinate system 132. For example, the device 102 is held by the robotic system 130 and its position is known in the robot coordinate system 132 using feedback from the robotic arm 134. In addition, an image of the device 102 with the marker device 104 is captured and can be registered with the position information from the robotic arm 134 to provide a position/orientation of the medical device 102 and the marker device 104 in the robot coordinate system 132. Registration is made between the robot coordinate system 132 and a coordinate system 138 of the scanning mechanism 111 (e.g., the X-ray C-arm coordinate system), imaging system 110 or other known reference. Registration techniques are known in the art.

Workstation 112 includes a display 118 for viewing images. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In one embodiment, the marker device 104 includes radio-opaque material 105 that is preferably configured to indicate a position and orientation of the marker device 104 despite different positions of the imaging system 110. In other words, the radio-opaque material 105 is configured to uniquely identify the position and orientation of the marker device 104 and therefore the medical instrument 102 no matter which angle the image is captured. The radio-opaque material 105 may include symbols, shapes, lines, dots, etc. The marker device 104 may include a radiolucent material on which the radio-opaque material 105 is formed or integrated.

Figure 2A:
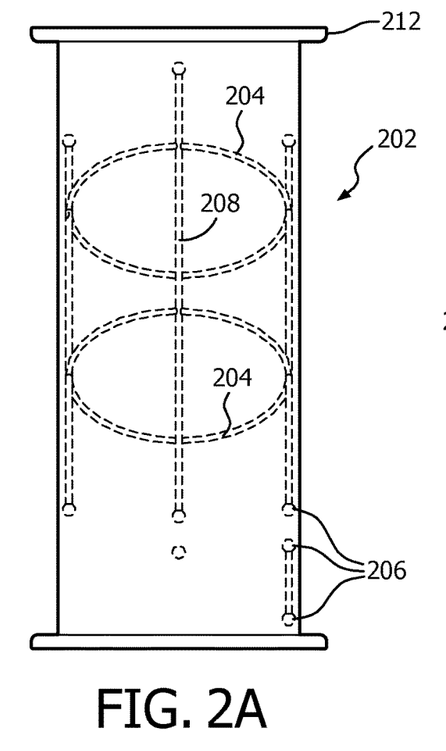
FIG. 2 is an anatomical section view showing a block/flow diagram showing remote center of motion points for medical instruments in accordance with one embodiment.
Figure 2B:
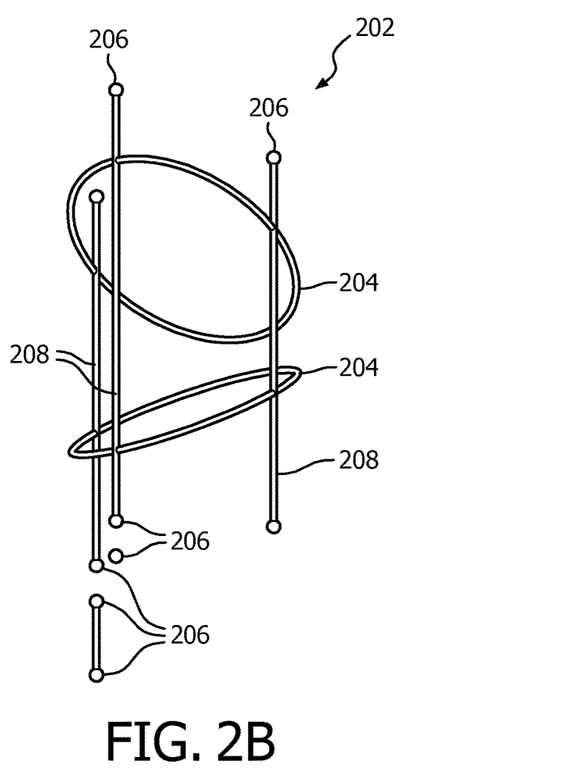

FIGS. 2A and 2B show two views of an illustrative design 202 with geometric features including shapes 204, dots 206, connecting lines 208, etc. in different configurations such that a single projection image can define the entire pose of the marker device 104 with respect to a C-Arm or imaging system coordinate system. It should be understood that a simpler design than design 202 may be employed but may need one or more 2D X-ray acquisitions to render its position, or need a 3D acquisition. FIG. 2A shows an X-ray projection of the design 202 having a cylindrical radiolucent wall 212 with the radio-opaque shapes 204 included therein or thereon. FIG. 2B shows a 3D rendering of the design 202.

Referring again to FIG. 1, the pose of the radio-opaque marker device 104 may be determined and described in the robot coordinate system 132. In accordance with the present principles, the marker device 104 is placed at a position that indicates or defines the remote center of motion (RCM). The marker position is then provided to the robot control software 136 by the registering of the marker position between the image coordinate system 138 and the robot coordinate system 132. When the instrument 102 is inserted in or through the marker device 104 by the robot 130, the control software 136 defines a virtual RCM 140 such that the robot system 130 is constrained by the location of the virtual RCM 140, hence constraining the motion of the instrument 102. For example, the robot arm 134 cannot be translated to advance the instrument any further into the port (104) or the like, but rotation may still be possible and may be partially constrained or unimpeded. The marker device 104 may be located at a pivot port site, be a part of the port or be included at another position where a RCM occurs or the RCM is likely to occur. The marker device 104 may be embedded with radio-opaque geometric shapes 105 that can render the pose of the port location in a single x-ray image.

Figure 3:
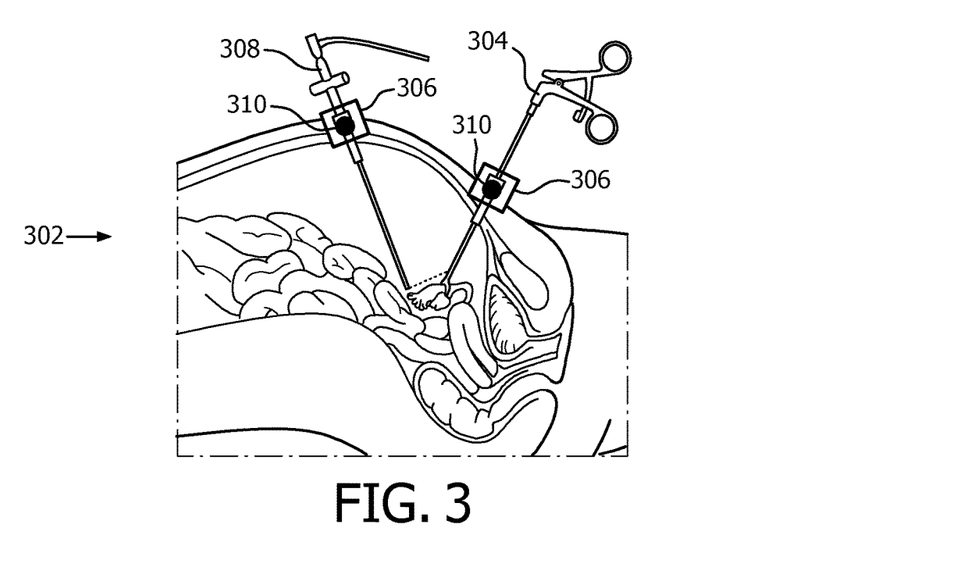
FIG. 3 is an illustrative configuration for radio-opaque material for use on a marker device in accordance with one embodiment.

Referring to FIG. 3, a section view of a patient or model 302 is depicted during minimally invasive surgery. Minimally invasive surgery is performed using elongated instruments 304 inserted into the patient's body 302 through small ports 306. A main visualization method during these procedures is an endoscope or laparoscope 308, which may be provided as instrument 102 or in addition to instrument 102 (FIG. 1). In robotic guided minimally invasive surgery, one or more of the instruments are held and controlled by the robot system 130 (FIG. 1). Small ports 306 that are placed on a patient's body 302 are the only incision points through which the instruments and endoscope may pass through to access the inside of the patient 302. As such, the instruments 304, 308 can rotate around these fulcrum points 310, but they cannot impose translational forces on the ports 306, as this may cause injury or harm to the patient 302.

In this example, the instruments 304 are inserted into two or more ports 306, and the robot guided endoscope 308 is inserted through another port 306. In other examples, the robot might hold one or more surgical instruments and/or the endoscope. If the robot system has a remote center of motion implemented in software, it may be necessary to indicate to the robot control software 136 (FIG. 1) where the location of a virtual remote center of motion is in the robot coordinate system 132, for the control software 136 to move the robot system 130 while not exerting forces on the fulcrum point 310 and causing tissue damage.

By defining a virtual RCM (e.g., in software) as a fulcrum point (310) or other position, the software enforces that only rotation (or other motion constraint, e.g., rotation on one or two dimensions only) can be performed at the port and all translational forces at that location are eliminated. This can be achieved by defining the virtual RCM at the position of a marker device(s) (ports 306) at a specific location which is defined using the registration between the imaging system and the robot system.

Figure 4:
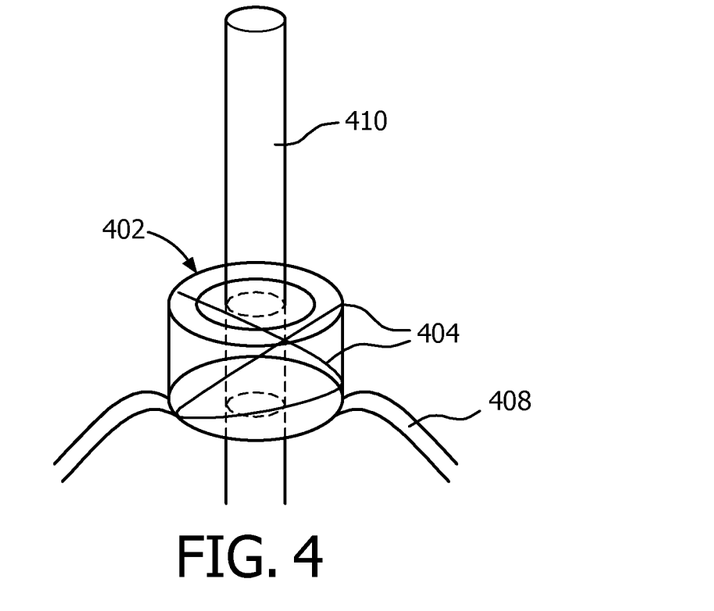
FIG. 4 is a perspective view of a trocar marker device in accordance with one embodiment.

Referring to FIG. 4, an illustrative embodiment is shown for a trocar marker device 402 in accordance with the present principles. The trocar marker device 402 includes radio-opaque shapes 404 attached or formed within or on the device 402 permitting X-ray image-based detection of a remote center of motion of a surgical instrument 410 held by a robot. The instrument 410 passes through at least a portion of the device 402. The position of the remote center of motion in the robot coordinate frame is assigned or provided by the placement of the trocar 402. The device 402 may be placed at a point of entry to a patient 408. This permits rapid and operator-independent detection of the remote center of motion from a single X-ray image. Determination of the RCM is one important aspect for safety of the patient during robotic manipulation of instruments.

The radio-opaque shapes 404 may be integrated in the device 402 to be detected in X-ray images. The shapes 404 may contain a series of geometric shapes, ideally lines, points and ellipses, which are embedded in the marker in a pre-determined configuration. These shapes 404 would be made of a contrasting material which has significantly distinct radio-opacity with its surrounding material. These shapes 404 preferably include a configuration such that a single projection image would be sufficient to define its entire pose and orientation. The geometric characteristics of these marker shapes 404 make it possible to describe the exact pose of a fiducial (e.g., 3 orientations and 3 translations) using a single X-ray image. Alternatively, the marker shapes 404 can have simple shapes (such as a sphere), however, it would require multiple X-ray images and thus while useful, is not the preferred embodiment. The radio-opaque marker 404 would come embedded in the trocar as a pre-manufactured part.

Figure 5:
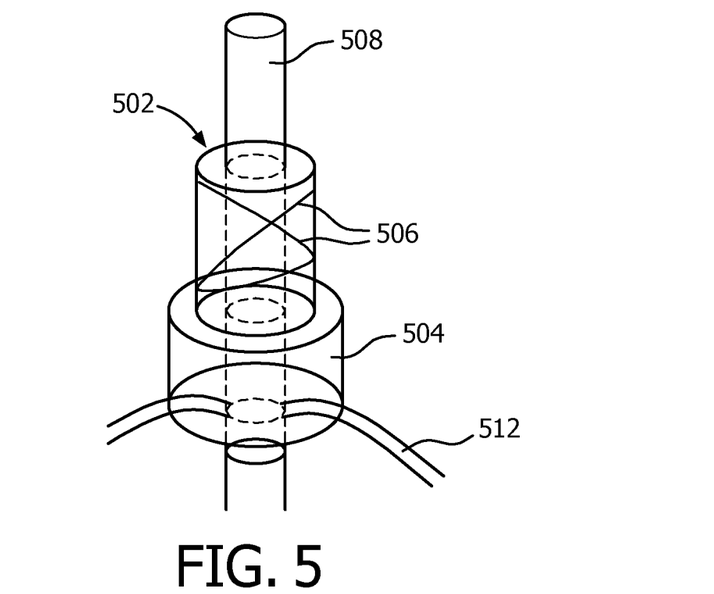
FIG. 5 is a perspective view of a separate marker device disposed on a trocar port in accordance with one embodiment.

Referring to FIG. 5, in this embodiment, a marker device 502 is not integrated in a trocar 504, but it is attached to either a surgical instrument/endoscope 508 or the trocar or port 504. As before, the marker device 502 may have a range of radio-opaque shapes and materials 506. In one embodiment, a marker device 502 with a hole therein is provided so that it can be located over a shaft of the instrument/endoscope 508 or on or in the trocar 504. The marker 502 may be located at the port/trocar 504 on a patient's skin 512. In one embodiment, the marker device 502 may include an adhesive strip or patch added to the port/trocar 504.

Figure 6:
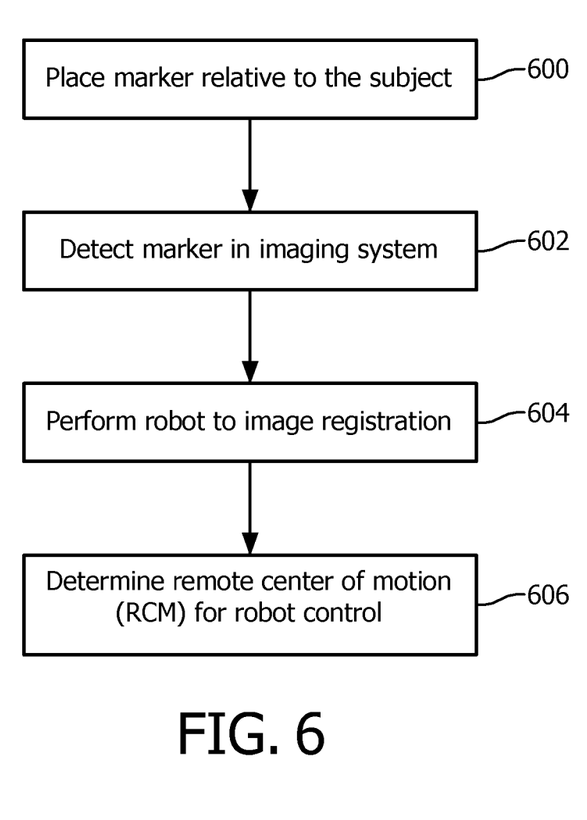
FIG. 6 is a flow diagram showing a method for defining a virtual remote center of motion for robotic control in accordance with an illustrative embodiment.

Referring to FIG. 6, a method to establish a position of a marker and RCM in a coordinate system of a robot is illustratively shown. In block 602, a detection of the marker in the imaging system (e.g., X-ray system) is performed. Detection of the position of the marker in X-ray coordinate system is done from an acquired X-ray image. Since, in one embodiment, the marker is radiolucent with radio-opaque markings, a simple thresholding method can segment the shape of the marker in the image. If the marker (e.g., trocar with markings) is designed to have a distinct shape, one X-ray image is sufficient to determine the exact position and orientation. If the marker has a simple shape (such as sphere) multiple images are needed and combined with known 3D pose calculation algorithms to define position, such as triangulation.

In block 604, robot to image system registration is performed. The registration between the robot coordinate frame and the X-ray C-arm coordinate frame is performed using known methods (e.g., fiducial markers, point to point registration, attaching the robot to a known location at the C-arm, etc.).

In block 606, a RCM position is provided or defined in the robot coordinate frame. The robot coordinate frame is known by establishing a relationship between the RCM position and the X-ray marker position. If the RCM marker is integrated in the trocar port then the relationship can be known by design. If the RCM marker is not integrated into the trocar port, then the distance between marker and trocar needs to be computed, by manual measurement or prior calibration. The motion control of the robot may include prevention of forward advancement of the instrument from the remote center of motion but permitting rotation (or limited rotation) of the instrument. Other motion constraints and controls may also be implemented.

The present embodiments can be used for different applications of robotically guided endoscopic minimally invasive surgery where x-ray imaging is available. The types of surgeries can include, but are not limited to cardiac surgery, minimally invasive coronary artery bypass grafting, atrial septal defect closure, valve repair/replacement, laparoscopic surgery, hysterectomy, prostatectomy, gall bladder surgery, natural orifice transluminal surgery (NOTES), pulmonary/bronchoscopic surgery, neurosurgical interventions, video assisted thoracic surgery, etc.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for localization of robotic remote center of motion point using a custom trocar (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for providing a virtual remote center of motion for robotic control, the system comprising:
a marker device configured to include one or more shapes that enable indication of position and orientation of the marker device in an image collected by an imaging system, the marker device being configured to receive or partially receive an instrument therein, the instrument being robotically guided by a robot system; and
a memory that stores:
a registration module configured to register a coordinate system of the imaging system with a robot coordinate system of the robot system, enabling use of the marker device to define a position of the virtual remote center of motion in the robot coordinate system; and
control software configured to control a motion of the robot system to robotically guide the instrument, wherein the virtual remote center of motion constrains the motion of the robot system.

2. The system as recited in claim 1, wherein the imaging system includes an intraoperative x-ray imaging system.

3. The system as recited in claim 2, wherein each of the one or more shapes comprises radio-opaque material and is integrally formed in the marker device.

4. The system as recited in claim 3, wherein the radio-opaque material of each of the one or more shapes is configured to identify the position and orientation of the marker device regardless of an angle from which the image is captured.

5. The system as recited in claim 2, wherein the one or more shapes are radio-opaque and formed in a separate part configured to engage one of the instrument and the marker device.

6. The system as recited in claim 1, wherein the control software prevents forward advancement of the instrument from the virtual remote center of motion but permits rotation of the instrument.

7. The system as recited in claim 1, wherein the system includes a surgical suite for performing a medical procedure.

8. The system as recited in claim 7, wherein the marker device includes a port for entry into a subject.

9. A marker for providing a virtual remote center of motion for robotic control that facilitates motion of one or more instruments, the marker comprising:
a radiolucent wall forming an internal cavity configured to receive or partially the one or more instruments; and
a radio-opaque material formed on or in the wall, the material being configured into one or more geometric shapes that enable indication of a three-dimensional orientation and position of the marker in an X-ray image such that the three-dimensional orientation and position provide the virtual remote center of motion for robotic control for the one or more instruments.

10. The marker as recited in claim 9, wherein the marker is integrally formed in a trocar.

11. The marker as recited in claim 9, wherein the marker includes a part configured to engage one of a medical port or a trocar.

12. A method for providing a virtual remote center of motion for robotic control, the method comprising:
   placing a marker at a location, the marker being configured to include one or more shapes;
   imaging the marker using an imaging system to obtain an image including the marker in a coordinate system of the imaging system, the one or more shapes included in the marker indicating position and orientation of the marker in the image;
   registering the coordinate system of the imaging system with a robot coordinate system of a robot system, and using the marker to define a position of the virtual remote center of motion in the robot coordinate system; and
   controlling a motion of an instrument robotically guided by the robot system, wherein the virtual remote center of motion constrains the motion.

13. The method as recited in claim 12, wherein the imaging system includes an X-ray imaging system.

14. The method as recited in claim 13, wherein the one or more shapes are radio-opaque and integrally formed in the marker.

15. The method as recited in claim 12, wherein controlling the motion includes preventing forward advancement of the robotically guided instrument from the remote center of motion, but permitting rotation of the robotically guided instrument.

16. The method as recited in claim 12, wherein the marker includes a separate part which contacts a port, and the method further comprising computing an offset between the port and the marker to provide the registering.

17. The method as recited in claim 12, wherein the robotically guided instrument is imaged along with the marker using the imaging system to obtain the image, which further includes the robotically guided instrument, in the coordinate system of the imaging system; and
   wherein the coordinate system of the imaging system is registered with the robot coordinate system of the robot system using a position of the robotically guided instrument.

* * * * *